United States Patent

Miller-Kovach et al.

[11] Patent Number: 6,040,531
[45] Date of Patent: Mar. 21, 2000

[54] PROCESS FOR CONTROLLING BODY WEIGHT

[75] Inventors: Karen Miller-Kovach, Centerport, N.Y.; Sarah May Watson, Camberley; Marian Jane Way, Fareham, both of United Kingdom; Wanema Frye, Overland Park, Kans.; Mary Grace Melnyk, Astoria; Adrienne Forman, Great Neck, both of N.Y.

[73] Assignee: Weight Watchers (UK) Limited, United Kingdom

[21] Appl. No.: 08/896,855

[22] Filed: Jul. 18, 1997

Related U.S. Application Data

[63] Continuation-in-part of application No. PCT/US96/17511, Nov. 1, 1996.

[30] Foreign Application Priority Data

Nov. 1, 1995 [GB] United Kingdom .................... 9522364

[51] Int. Cl.[7] .................................................. G06F 15/02
[52] U.S. Cl. .................. 177/25.16; 128/921; 364/709.03
[58] Field of Search ......................... 128/921; 177/25.16; 364/709.03

[56] References Cited

U.S. PATENT DOCUMENTS

| | | | |
|---|---|---|---|
| 4,796,182 | 1/1989 | Duboff | 364/709.03 |
| 4,951,197 | 8/1990 | Mellinger | 364/709.03 |
| 5,412,560 | 5/1995 | Dennision | 128/921 |
| 5,704,350 | 1/1998 | Williams, III | 128/921 |
| 5,796,640 | 8/1998 | Sugarman et al. | 364/709.03 |

FOREIGN PATENT DOCUMENTS

| | | |
|---|---|---|
| 2714500 | 6/1995 | France . |
| 59-142657 | 8/1984 | Japan . |
| 2288257 | 10/1995 | United Kingdom . |
| WO93/07570 | 4/1993 | WIPO . |
| WO97/16791 | 5/1997 | WIPO . |

OTHER PUBLICATIONS

Dietary Guidelines for Americans, U.S. Deptartment of Agriculture, U.S. Department of Health and Human Services, 1995.

Live Well The Low–Fat/High–Fiber Way, the American Health Foundation No Date Given.

Fat & Fiber Plan, Weight Watchers International, Inc., 1966.

*Primary Examiner*—Randy W. Gibson
*Attorney, Agent, or Firm*—Burns, Doane, Swecker & Mathis LLP

[57] ABSTRACT

The disclosure relates to a process for controlling body weight in which selection of food servings is based on a calculated point value and a range of allotted daily POINTS which is adjusted for weight change. The calculated POINT value is a function of measured calories, total fat and dietary fiber for serving sizes specified in readily estimatable units.

17 Claims, 9 Drawing Sheets

PROCESS FOR CONTROLLING BODY WEIGHT

RELATED APPLICATIONS

This is a continuation-in-part of PCT/US96/17511 filed Nov. 1, 1996 which designated the United States and claimed priority to GB 9522364.0 filed Nov. 1, 1995. The PCT application is entitled "SLIMMER'S CALCULATOR" and corresponds to International Publication No. WO 97/16791, dated May 9, 1997 which is incorporated herein by reference.

FIELD OF THE INVENTION

The present invention relates to processes for assisting persons in weight control or weight loss.

BACKGROUND AND OBJECTS OF THE INVENTION

It is widely recognized that diet is important to the health and psychological well being of human beings. Choice of types and amounts of food is an important factor in maintaining or modifying body weight.

Weight reduction diets have become extremely popular and many regimes have been proposed. Many such regimes are based on the simple proposition that in order to lose weight, a person must eat food having fewer calories than she/he requires. The number of calories required by an individual is determined by his/her weight and level of activity. A heavy or active person requires more calories than a light or inactive person.

In order to establish the number of calories that a person requires in a day to support her/his energy demand, a value, termed the basal metabolic rate (BMR), is multiplied by a factor determined by the activity level of the person. The value of the BMR is dependent on the sex and weight of a person and tables of this data are readily available to those skilled in the art of dietetics.

When a person is following a conventional calorie intake restriction diet (known colloquially as "counting calories"), his/her daily calorie demand is determined from her/his BMR and activity level. For instance, a moderately active woman weighing 60 kg would have a BMR of 5565 kJ/day and an activity factor of 1.3 giving a daily requirement of 7234 kJ. In order for this person to lose 0.45 kg (1 lb) in one week, her daily calorie intake must be restricted to 5142 kJ.

The present inventors have established that merely "counting calories" is not ideal and that other factors should be taken into account. However, taking into account additional factors requires the dieter to perform more complex mathematics which is difficult in the bustle of daily life.

It is an aim of the present invention to provide an apparatus whereby a diet regime, more complex than mere "calorie counting", can be readily implemented.

Various health organizations have provided dietary guidelines, which take into account health and weight considerations. For example, the U.S. Department of Agriculture and Department of Health and Human Services issued "Dietary Guidelines for Americans in 1995". The recommendations include eating a variety of foods and decrease of caloric intake. A diet low in saturated fat, and cholesterol is recommended, as is an increase in consumption of grains, fruits and vegetables. Other writers in the field have focused on the benefits of low fat/high fiber diets. See, e.g., "Live Well The Low-Fat/High-Fiber Way", a food plan of the American Health Foundation. While such studies and publications provide detailed analysis of some foods, it is difficult for an average individual to implement these recommendations.

These difficulties have been addressed by detailed programs developed by health professionals. One such plan is the FAT and FIBER PLAN developed by Weight Watchers International, Inc. The plan provides daily guides, food lists and menu ideas. A minimum number of fiber grams and a maximum number of fat grams are allotted each day. Food labels used to gather nutrition information and implementation of the plan involves use of a "tracker" to tally the fat and fiber grams, units of food in the various categories and bonus calories in the foods consumed during the day.

In spite of the value and success of such a plan, there is a need for a weight control or modification process which is more simply and easily implemented by the individual, while accounting for current dietary recommendations of health authorities.

Accordingly, it is an object of the present invention to provide a dietary control process which accommodates a wide variety of food preferences, current body weights, body weight objectives, food properties and serving sizes.

It is a further object of the present invention to provide a process of food selection which is easily mastered by an individual seeking to maintain or modify his or her body weight.

It is a further object of the present invention to provide a process of food selection which involves minimal study, computation and record keeping by an individual seeking to maintain or modify his or her body weight.

It is a further object of the present invention to express the dietary contribution of each of a wide variety of food servings into a single numerical value, and use those values in an easily implemented plan of body weight management.

It is a further object of the present invention to provide mechanisms for the easy computation of such a single numerical value, based on various nutritional characteristics of a wide variety of food servings.

These and other objects and features will be apparent from the following description of the subject invention.

SUMMARY OF THE INVENTION

The present invention includes processes for controlling the body weight of a human being. As used herein "control" of body weight may involve weight reduction, weight gain or current weight maintenance.

In preferred embodiments of the present invention, dietary properties, such as calories, fat and fiber, of candidate food servings are measured. A POINT value P for each candidate food serving is calculated in accordance with an algorithm which takes into account dietary contributions of each. A range of total POINTS allotted per day is determined based on current body weight. During a day, food servings are selected for consumption having a total POINT value within the range. The steps are repeated in successive days to achieve the desired weight control. If body weight changes, the total daily allotted POINTS are adjusted to maintain an appropriate nutritional baseline.

In accordance with the present invention, a calculator may be provided for assisting a person on a diet regime wherein said person is allocated a maximum daily POINTS target, said POINTS being related to the caloric value and another nutritional parameters of food ingested, the calculator comprising means for inputting a first number related to the caloric value of a food item, means for inputting a second number related to another parameter of the food item, display means and processing means programmed to perform an algorithm so as to process said numbers to produce a resultant POINTS value and to control the display to display said resultant POINTS value.

Preferably, the another selected parameter is saturated fat content, but the present invention is not restricted thereto. For example, the simple sugar content of foodstuff may be used as an alternative or additionally.

In one embodiment, the algorithm is:

$$p = \frac{c}{k_1} + \frac{f}{k_2}$$

where p is the resultant POINTS value, c is the caloric value related number, f is the number related to the other parameter, and $k_1$ and $k_2$ are constants. The value c may be a kilojoules or kilocalories and the constant $k_1$ is chosen so that the POINTS target will be in the low tens. Numbers in the low tens are easier for people to deal with than the numbers in the thousands which "calorie counting" involves. If the value c is to be entered in kilocalories, $k_2$ is preferably within the range $k_1/35$ to $k_1/10$, more preferably $k_1/17.5$. However, if the value c is to be entered in kilojoules, $k_2$ is preferably in the range $k_1/146.7$ to $k_1/41.8$, more preferably $k_1/72.8$. The values for $k_2$ are based on the assumption that f is in grams. Suitable scaling factors will be needed if f is in other units. Conveniently, the resultant POINTS value will be rounded up or down to an integer value. However, values in the range 0.25 to 0.74999 may be rounded to 0.5 and values below 0.25 rounded to 0.0.

An alternative algorithm is:

$$p = \frac{c}{k_1} + \frac{f}{k_2} - \frac{r}{k_3}$$

In this algorithm, f represents total fat content and r represents the weight of roughage or dietary fiber in a portion of food. If the value c is entered in kilocalories, $k_2$ is preferably in the range $k_1/4.5$ to $k_1/1.5$, more preferably in the region of $k_1/4$. If the value c is entered in kilocalories, $k_3$ is preferably in the range $k_1/20$ to $k_1/5$, more preferably in the region of $k_1/10$. The values for $k_2$, and $k_3$ are based on the assumption that f and r are in grams. Suitable scaling factors will be needed if f or r is in other units.

Conveniently, the processing means of the aforementioned calculator is operable to accumulate or sum said resultant POINTS value. In this way, the calculator can inform a user of the POINTS used or still available in a day.

Prepackaged food in many countries is labelled with the calorie, saturated fat and dietary fiber content and a user may employ this data in practicing the present invention. In preferred embodiments of the present invention, POINT values are calculated by the manufacturer and printed on the packaging of the food serving. However, when food is sold loose or served in a restaurant, this information is not available. In order to solve this problem, the calculator may include memory means storing a database of data related to the caloric value and one or more other parameters of a plurality of foodstuffs. Thus, a user will be able to obtain the necessary data by identifying the foodstuff and its quantity. In another embodiment, a slide rule is provided for calculating POINT values. In a further alternative, POINT values, calculated according to the algorithm, are provided in tabular form for serving sizes specified in readily estimatable of units.

DESCRIPTION OF PREFERRED EMBODIMENTS

Figure 1:
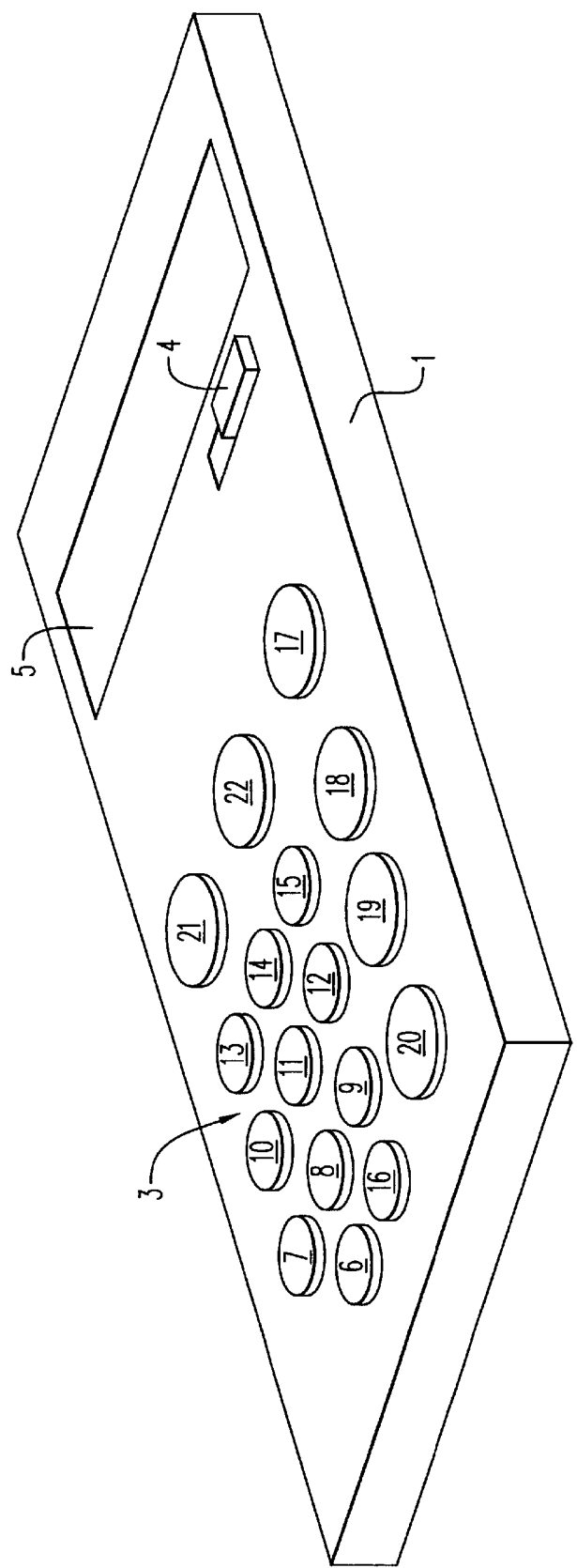
FIG. 1 shows a first embodiment of a calculator for practicing the present invention.

Embodiments of the present invention will now be described, by way of examples.

In accordance with preferred embodiments of the present invention, POINTS are assigned to candidates food servings of readily estimated or predetermined portion size. For example, a fist sized portion of whole fruit is equal to about one cup; a thumb sized portion of cheese or meat is equal to about one ounce. For such serving sizes, a determination is made of calories (kilocalories), c, total fat in grams, f and/or dietary fiber in grams r. A POINT value p for each food serving is calculated for each food serving in accordance with a formula. In a preferred embodiment of the present invention the formula is $$p = \frac{c}{k_1} + \frac{f}{k_2} - \frac{r}{k_3} \tag{1}$$

where $k_1$=50, $k_2$=12 and $k_3$=5. Advantageously, the POINTS, p, are small, whole numbers and are calculated for many common foods and serving sizes. The whole numbers are obtained by rounding up at 0.50. The values of the constants $k_1$, $k_2$ and $k_3$ were empirically derived from data obtained from nutritional studies conducted by Weight Watchers International.

By use of the foregoing formula, total fat becomes a POINT penalizer and dietary fiber a POINT ENHANCER. THE USER MAY OBTAIN THE POINT value by calculation of POINTS, either by slide rule or calculator. Alternatively the POINT value may be obtained by the consumer from lists or packaging, the calculations having been done by the list-maker or food packager. In any of these cases, the POINT value is transparent to the consumer and corresponds with perceived views in the U.S. of the benefit of dietary fiber and the value of avoiding dietary fat. The overall POINT value assigned to each food reflects this weighting.

In variations of the formula (1), the r term may be eliminated, and $k_1$ set equal to 70 and $k_2$ set equal to 4. Such an approach may be more appropriate for dieters who do not recognize the value of fiber in the diet and for whom saturated fat is more prevalent. Other variations of the formula (1) are discussed below.

In preferred embodiments of the claimed invention, a range of POINTS allotted per day is determined based on current body weight. Advantageously, this range of POINTS is seven POINTS from minimum to maximum. The appropriate ranges of POINTS are assigned to each of series of weight ranges. In particular when the formula (1) is used with the above-mentioned values of k, the range of POINTS allotted per day may be determined in accordance with the following table:

| Current Body Weight | Range Of Points Allotted Per Day |
|---|---|
| Less than 150 pounds | 18–25 |
| 150 to 174 pounds | 20–27 |
| 175 to 199 pounds | 22–29 |
| 200 to 224 pounds | 24–31 |
| 225 to 250 pounds | 26–33 |
| Over 250 pounds | 28–35 |

In other preferred embodiments, food servings having a total number of POINTS equal to at least the range minimum are ingested each day, thus providing adequate minimum calories. Unused POINTS up to a predetermined maximum may be carried over to another day within the week. This feature has important psychological benefits, in that it permits the dieter to accommodate an occasional meal or treat which would otherwise violate the daily maximum, while providing long term control over food intake.

In other preferred embodiments, POINTS may be added to the maximum daily POINT total on the basis of performance of a predetermined amount of physical exercise during the day in question. For example, one bonus POINT may be added for each 20 minutes of moderate physical exercise such as ballroom dancing, walking, canoeing, etc.

The POINT values for each food serving may be calculated in a variety of ways. They may be manually calculated by the individual whose weight is to be controlled based on nutritional information provided on food packages. Alternatively the POINTS may be obtained electronically by retrieving point values from an electronic memory or calculating POINTS from input values of c, f and r as described in greater detail below.

Referring to FIG. 1, a calculator for implementing the processes of the present invention is physically similar to a conventional calculator and comprises a housing 1, a keypad 3, an on/off switch 4 and an alphanumeric display 5. The keypad 3, however, is tailored to the calculator's particular function and comprises keys 6 through 15 for numbers 0 to 9, key 16 for the decimal point, a calories (CAL) key 17, a saturated fats (SAT FAT) key 18, a calculate (POINTS) key 19, an accumulate (STORE) key 20, a clear (CLEAR) key 21 and a new day (NEW DAY) key 22.

Figure 2:
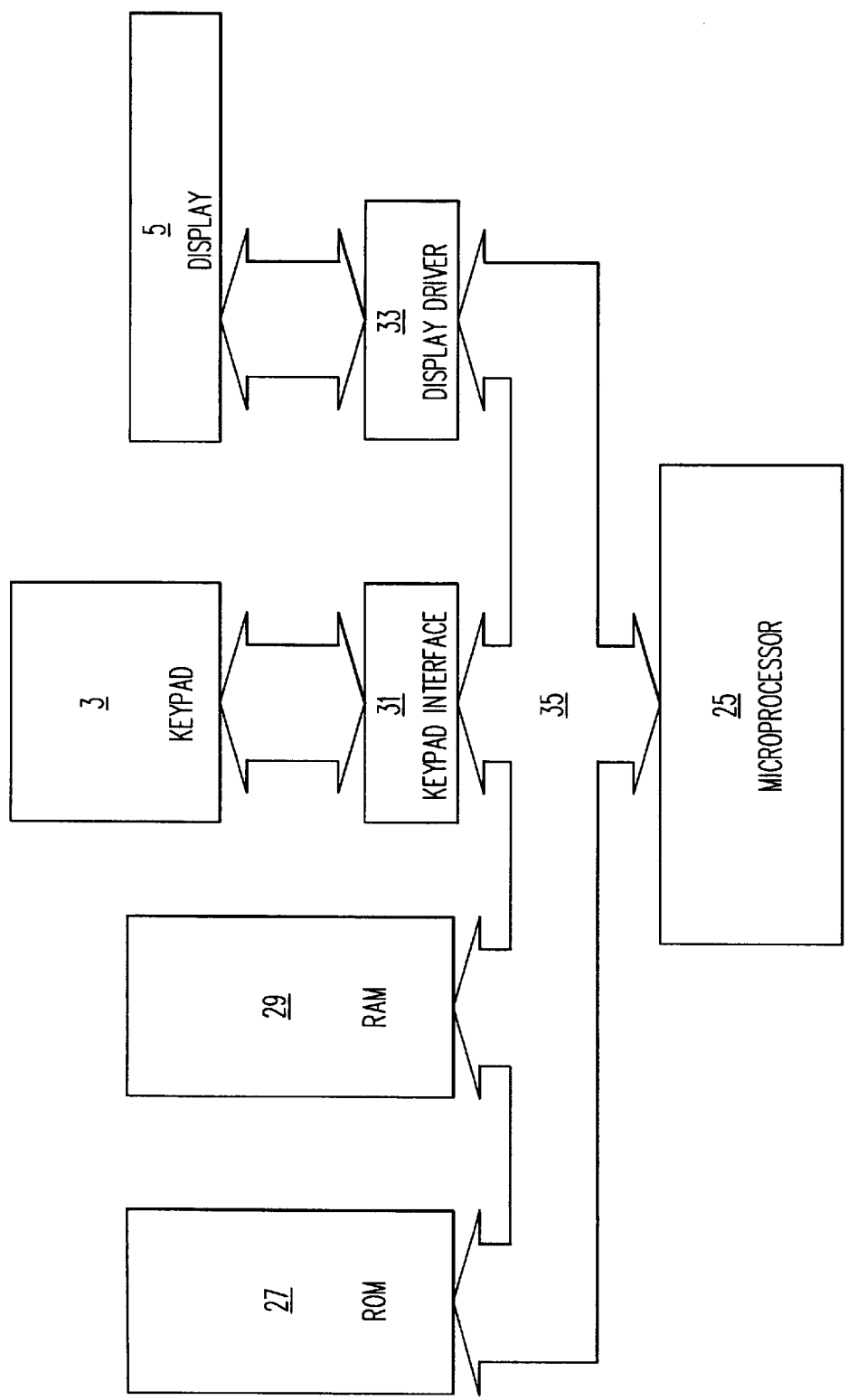
FIG. 2 is a block diagram of the electronic circuitry of a calculator for practicing the present invention.

Referring to FIG. 2, the electronic circuitry of the calculator comprises a microprocessor 25, a ROM 27, a RAM 29, a keypad interface circuit 31, a display driver circuit 33 and a bus 35 which interconnects the active components. The keypad interface circuit 31 is coupled to the keypad 3 and detects key presses and notifies the microprocessor 25 of the operation of any of the keys 6 through 22. The display driver circuit 33 controls the display in response to commands from the microprocessor 25. The ROM 27 stores the control program for the microprocessor 25 and constants used in calculations, and the RAM 29 is used to store data input by a user, the results of calculations and intermediate values. The RAM 29 is of a non-volatile type or is provided with power independently of the main on/off switch 4.

The operation of the calculator shown in FIG. 1 will now be described. In the following, description of the control of the display 5 in direct response to key presses will be omitted for the sake of clarity. However, it will be appreciated that the microprocessor 25 will control the display 5, via the display driver circuit 33, to indicate to a user that a key 6 through 22 has been fully pressed. Operation of the number and decimal point keys 6 through 16 will result in the display of numbers in the manner of a conventional calculator. Operation of the other keys will be indicated by a suitable descriptive word, e.g. NEW DAY, POINTS, STORING etc.

Figure 3:
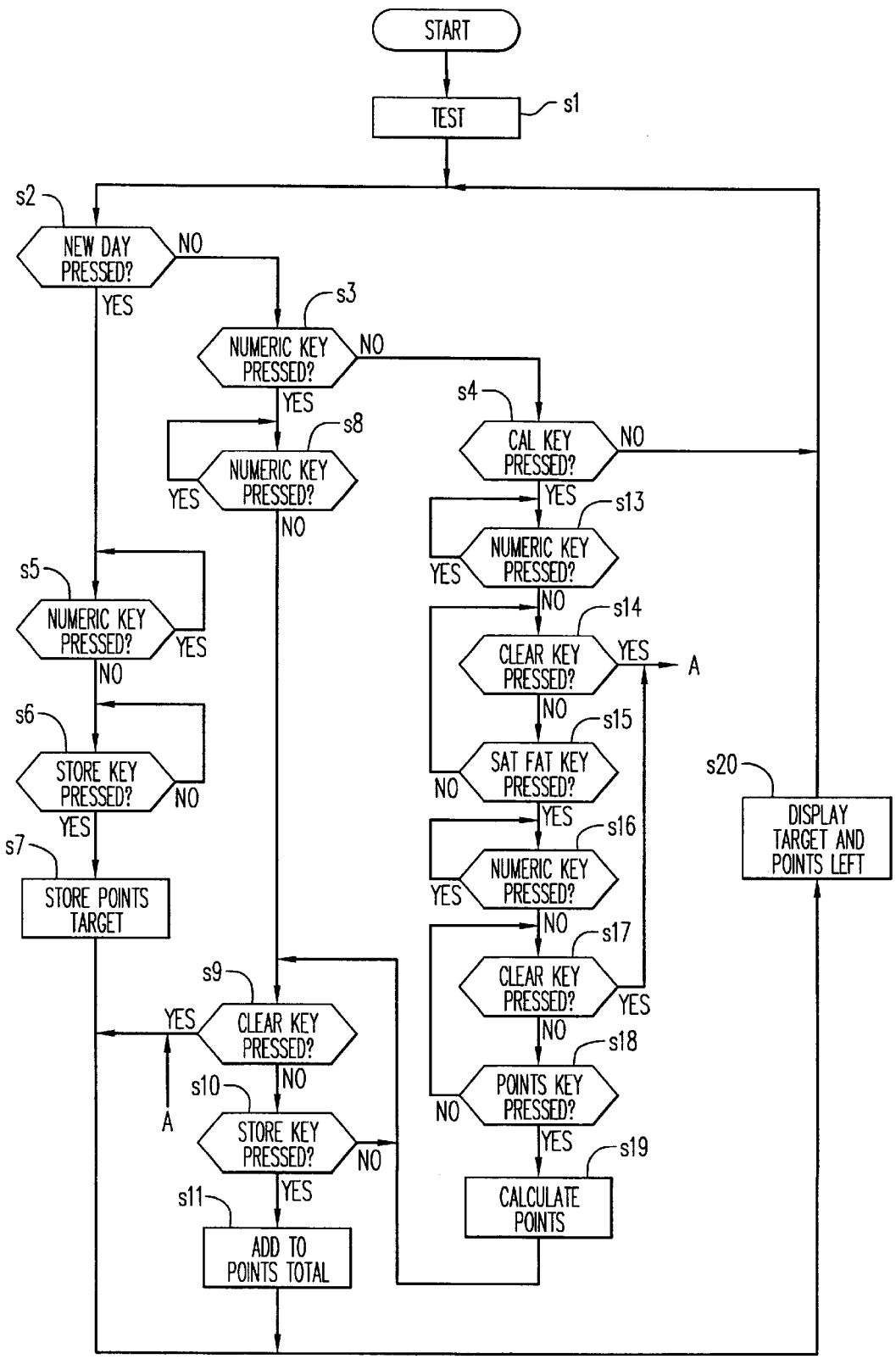
FIG. 3 is a flow diagram illustrating the operation of the calculator of FIG. 1.

Referring to FIG. 3, when the calculator is switched on, it performs a self test routine s1 during which target and current POINTS left values in the RAM 29 are displayed on the display 5 with the messages "TARGET" and "POINTS LEFT TODAY" respectively. If the self test routine s1 reveals no faults, the microprocessor 25 loops through three keypress test steps comprising "is the NEW DAY key 22" being pressed s2, "is a number or decimal POINT key 6 through 16" being pressed for direct entry of POINTS 53 and "is the CAL key 17" being pressed for calculation of POINTS 54.

If it is determined, at step s2, that the NEW DAY key 22 is being pressed, the microprocessor 25 performs step s5. At step s5, the microprocessor 25 repeatedly determines whether a numerical key 6 through 16 is being pressed to enable the user to enter his/her POINTS target for the day. If a key other than a numerical key 6 through 16 is being pressed, step s6 is performed. At step s6, the microprocessor 25 determines whether the STORE key 20 is being pressed. If not, the microprocessor 25 repeatedly interrogates the keypad interface circuit 31 until it has been pressed. When the STORE key 20 is pressed, the microprocessor 25 performs step s7. At step s7, the microprocessor 25 stores the input POINTS target, or restores the previous value if no numerical keys 6 through 16 have been pressed, in the RAM 29, and sets an accumulated POINTS value, stored in the RAM 29, to zero. The display 5 is then updated at step s20, to show the messages "TARGET n" and "POINTS LEFT TODAY n—accumulated POINTS value", where n is the target value.

If it is determined, at step s3, that a number or decimal point key, that is a numerical key, 6 through 16 is being pressed, the microprocessor 25 moves on to step s8. At step s8, the microprocessor 25 determines whether additional numerical keys 6 through 16 are being entered. Once a key other than a numerical key 6 through 16 is pressed, the microprocessor 25 moves on to step s9 where it determines whether the CLEAR key 21 is being pressed. If the CLEAR key 21 is not being pressed, the microprocessor 25 determines whether the STORE key 20 is being pressed at step s10. If the STORE key 20 is not being pressed, the microprocessor 25 returns to step s9.

If the STORE key 20 is being pressed, the microprocessor 25 performs step s11 where the entered number is added to the accumulated POINTS total stored in the RAM 29. Finally, the target and POINTS left values are displayed at step s20.

If it is determined, at step s4, that the CAL key 17 is being pressed, the microprocessor 25 repeatedly performs a number entry step, step s13, until a non-numeric key is pressed. This enables a user to enter the calorie value for an item of food. When this occurs, the microprocessor 25 determines whether it is the CLEAR key 21 which is being pressed, step s14. If the CLEAR key 21 is not being pressed, the microprocessor 25 determines whether the SAT FAT key 18 is being pressed, step s15. If the answer at step s15 is no, the microprocessor 25 returns to step s14.

Once the SAT FAT key 18 has been pressed, the microprocessor 25 performs another number entry step, step s16.

This enables a user to enter the quantity in grams of saturated fats for the food item. At step s17, the microprocessor 25 determines whether the CLEAR key 21 is being pressed. If the CLEAR key 21 is not being pressed, the microprocessor 25 performs step s18 to determine whether the POINTS key 19 is being pressed. If the POINTS key 19 is not being pressed, the microprocessor 25 returns to step s17. If, however, the POINTS key 19 is being pressed, the microprocessor 25 performs step s19. At step s19, the microprocessor 25 calculates the POINTS for the food item according to the equation:

$$p = \frac{c}{70} + \frac{f}{4}$$

where p is the POINTS value, c is the number of kilocalories entered and f is the number of grams of saturated fat entered. The microprocessor 25 then causes the display driver 33 to display the POINTS value on the display 5.

Once the POINTS value has been displayed, the microprocessor 25 moves to step s9. If, for instance, the displayed POINTS value is greater than the POINTS left for the user for the current day, the user may not eat the food item and can press the CLEAR key 21.

After step s20 is performed, the microprocessor 25 reenters the loop of steps s2, s3 and s4.

Another embodiment of the present invention will now be described, with reference to FIGS. 2, 4 and 5.

Figure 4:
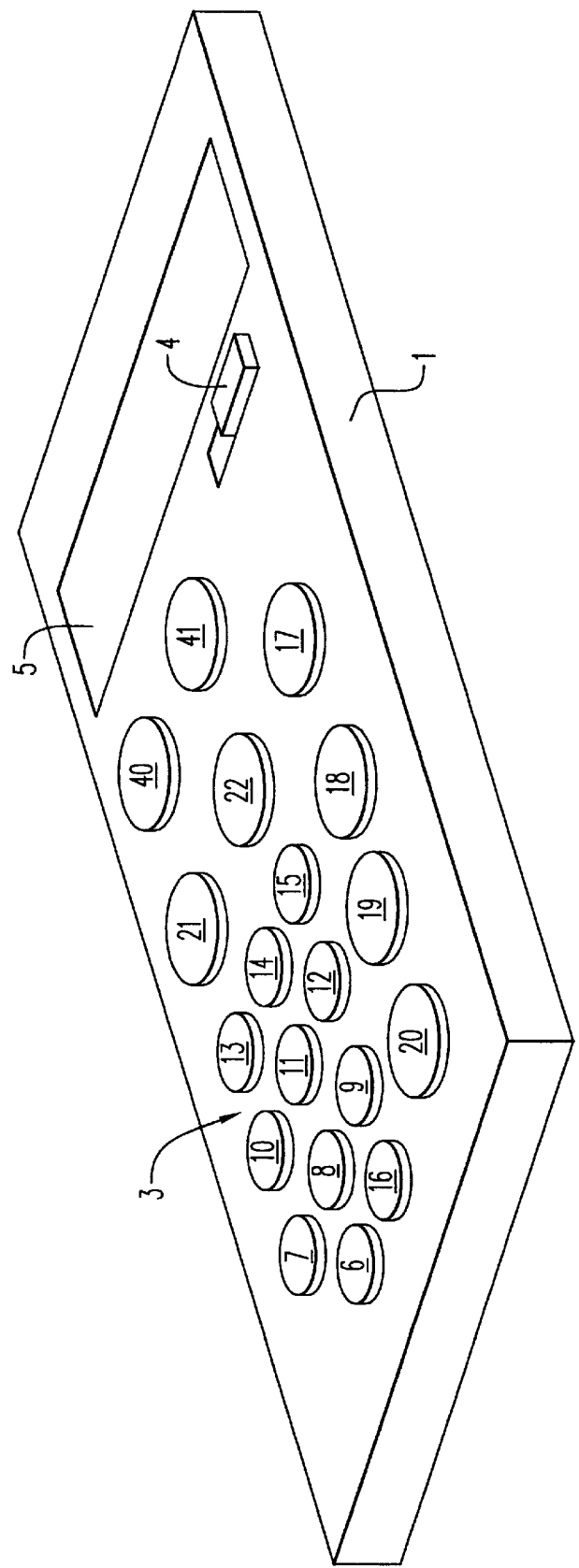
FIG. 4 shows a second embodiment of a calculator for practicing the present invention.
Figure 5:
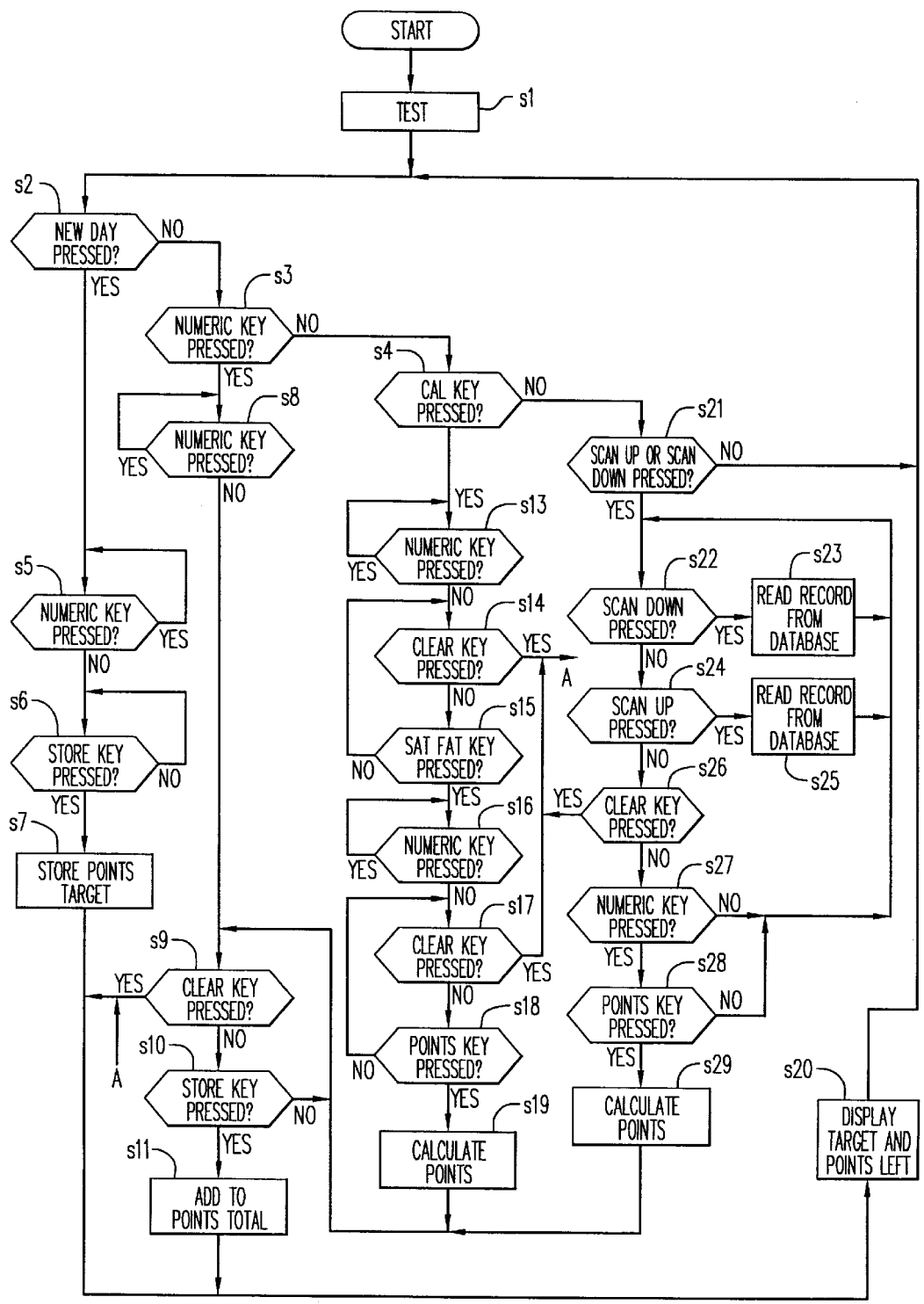
FIG. 5 is a flow diagram illustrating the operation of the calculator of FIG. 4.

Referring to FIG. 4, a dieter's calculator is substantially the same as the embodiment described above and the same features are indicated with the same reference numbers. However, this embodiment is provided with a SCAN UP key 40 and a SCAN DOWN key 41. These keys are used in conjunction with a database of POINTS values for different food items stored in the ROM 27 (FIG. 2) to enable a user to use the calculator when the calorie and saturated fat values for a food item are not available, for instance when eating in a restaurant.

The operation of the calculator, shown in FIG. 4, will now be described with reference to FIG. 5.

The operation of the calculator of FIG. 4 is that same as that of the calculator of FIG. 1 except for the addition of a step, step s21, to the keypress test loop and an associated routine. If the answers to the tests at steps s2, s3 and s4 are all no, the microprocessor 25 determines whether the SCAN UP key 40 of the SCAN DOWN key 41 is being pressed. If one of these keys is being pressed, the microprocessor 25 first tests whether it is the SCAN DOWN key 41 which is being pressed at step s22. If the SCAN DOWN key 41 is being pressed, the microprocessor 25 reads the first record from the database in the ROM 27 and causes it to be displayed (step s23). The display 5 will comprise an identification of a food item, a number of POINTS and the unit to which the POINTS relate, for instance BANANA 1 EACH, STEAK 2 100 G or COLA 1 100 ML. Then the microprocessor 25 returns to step s22.

If it is not the SCAN DOWN key 41 which is being pressed, the microprocessor 25 confirms that the SCAN UP key 40 is being pressed. If this is the case, the microprocessor 25 performs step s25 which comprises causing the last item in the database to be displayed on the display 5. Then the microprocessor 25 returns to step s22.

If the SCAN UP key 40 or the SCAN DOWN key 41 is being pressed at this time, the microprocessor 25 moves to step s23 or step s25 as appropriate. However, on this occasion, the preceding or succeeding database entry will be displayed, depending on which key is being pressed.

If neither the SCAN UP key 40 nor the SCAN DOWN key 41 is being pressed, the microprocessor 25 determines whether the CLEAR key 21 is being pressed. If the CLEAR key 21 is not being pressed, the microprocessor 25 moves on to step s27 where it determines whether a numerical key 6 through 16 is being pressed. If a numerical key 6 through 16 is being pressed, the microprocessor 25 returns step s22. Otherwise, the microprocessor 25 moves on to step s28 where it determines whether the POINTS key 19 is being pressed. If not, the microprocessor 25 returns to step s22. However, if it is, the microprocessor 25 performs step s29. At step s29, the microprocessor 25 multiplies the POINTS value for the last displayed database entry by the number entered by the user. The result is displayed on the display 5. Next, the microprocessor 25 moves to step s9.

A further embodiment of the present invention will now be described, with reference to FIGS. 2, 6 and 7.

Figure 6:
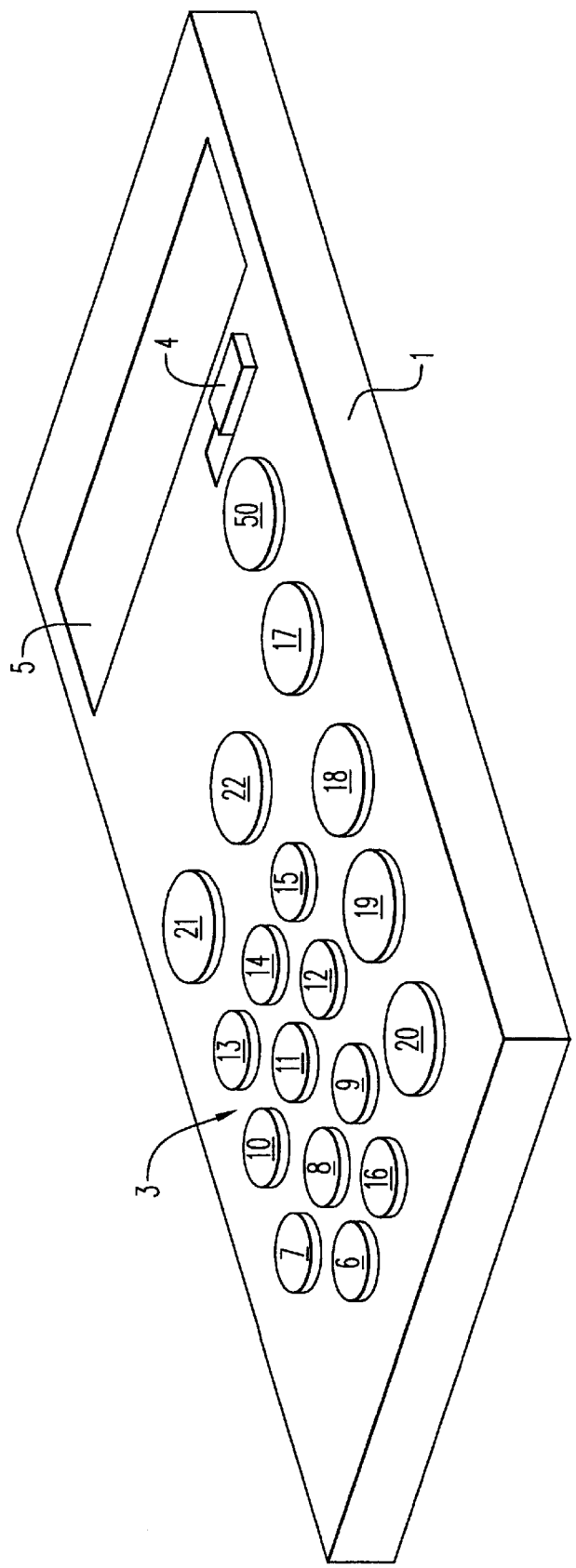
FIG. 6 shows a third embodiment of a calculator for practicing the present invention.

Referring to FIG. 6, the dieter's calculator is substantially the same as in the first embodiment described above and the same features are indicated with the same reference numbers. However, this embodiment is provided with a dietary fiber (FIBER) key 50 and the SAT FAT key 18 is now a FT key. This key is divided so that a user can enter the weight of dietary fiber in a portion of food.

The operation of the calculator, shown in FIG. 6, will now be described with reference to FIG. 7.

Figure 7:
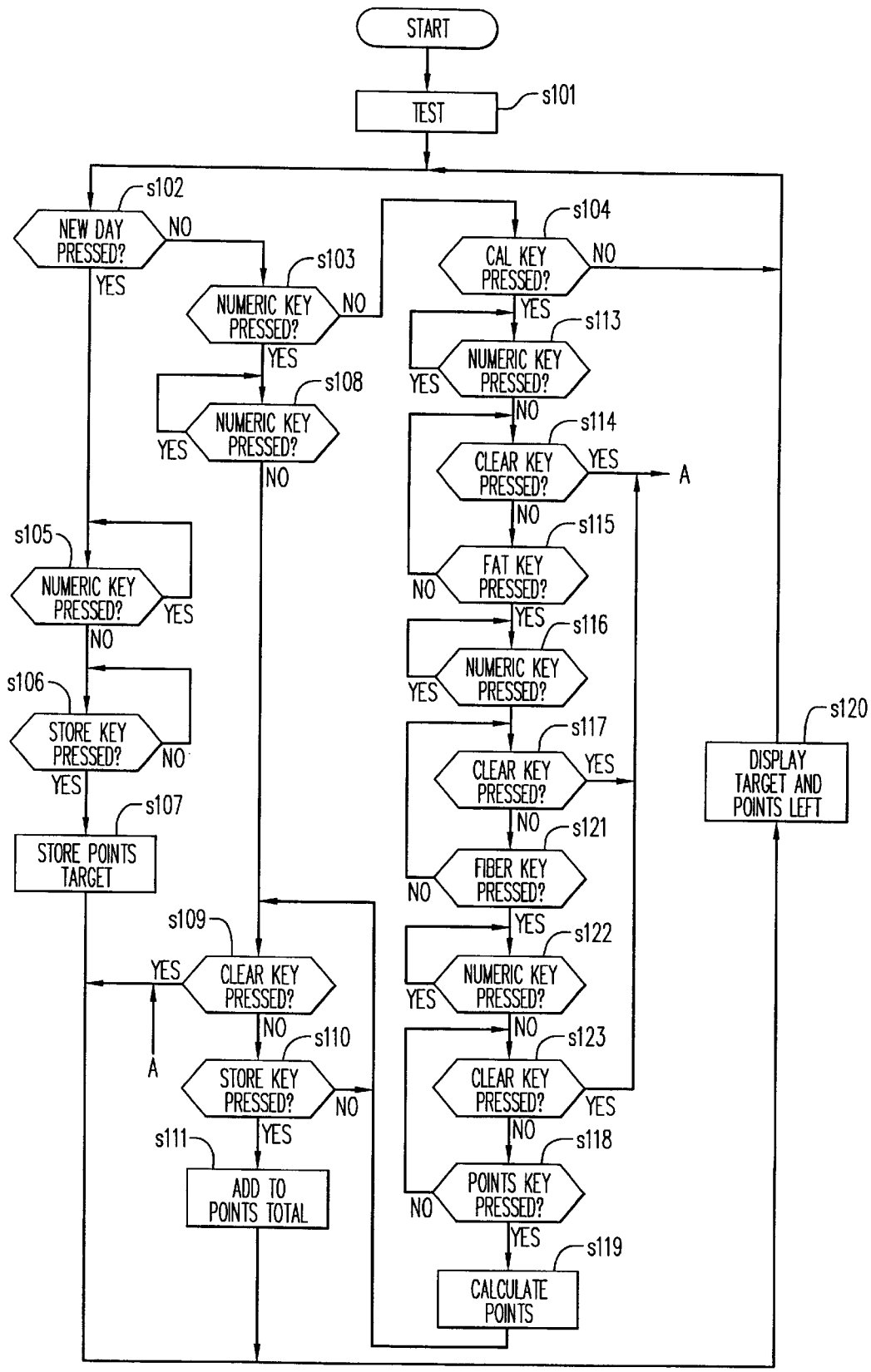
FIG. 7 is a flow diagram illustrating the operation of the calculator of FIG. 5.

Referring to FIG. 7, when the calculator is switched on, it performs a self test routine s101 during which targets and current POINTS left values in the RAM 29 are displayed on the display 5 with the messages "TARGET" and "POINTS LEFT TODAY" respectively. If the self test routine s101 reveals no faults, the microprocessor 25 loops through three keypress test steps comprising "is the NEW DAY key 22" being pressed s102, "is a number or decimal point key 6 through 16" being pressed for direct entry of POINTS and "is the CAL key 17" being pressed for calculation of POINTS.

If it is determined, at step s102 that the NEW DAY key 22 is being pressed, the microprocessor 25 performs step s105. At step s105, the microprocessor 25 repeatedly determines whether a numerical key 6 through 16 is being pressed to enable the user to enter his/her POINTS target for the day. If a key other than a numerical key 6 through 16 is being pressed, step s106 is performed. At step s106, the microprocessor 25 determines whether the STORE key 20 is being pressed. If not, the microprocessor 25 repeatedly interrogates the keypad interface circuit 31 until it has been pressed. When the STORE key 20 is pressed, the microprocessor 25 performs step s107. At step s107, the microprocessor 25 stores the input target, or restores the previous value if no numerical keys 6 through 16 have been pressed, in the RAM 29, and sets an accumulated POINTS value, stored in the RAM 29, to zero. The display 5 is then updated at step s120, to show the messages "TARGET n" and "POINTS LEFT TODAY n—accumulated POINTS value", where n is the target value.

If it is determined, at step s103, that a number or decimal point key, that is a numerical key, 6 through 16 is being pressed, the microprocessor 25 moves on to step s108. At step s108, the microprocessor 25 determines whether additional numerical keys 6 through 16 are being entered. Once a key other than a numerical key 6 through 16 is pressed, the microprocessor 25 moves on to step s109 where it determines whether the CLEAR key 21 is being pressed. If the CLEAR key 21 is not being pressed, the microprocessor 25 determines whether the STORE key 20 is being pressed at step s110. If the STORE key 20 is not being pressed, the microprocessor 25 returns to step s109.

If the STORE key 20 is being pressed, the microprocessor 25 performs step s111 where the entered number is added to the accumulated POINTS total stored in the RAM 29. Finally, the target and POINTS left values are displayed at step s120.

If it is determined, at step s104, that the CAL key 17 is being pressed, the microprocessor 25 repeatedly performs a number entry step, s113, until a non-numeric key is pressed. This enables a user to enter the calorie value of an item of food. When this occurs, the microprocessor 25 determines whether it is the CLEAR key 21 that is being pressed, step s114. If the CLEAR key 21 is not being pressed, the microprocessor 25 determines that the FAT key 18 is being pressed, step s115. If the answer at step s115 is no, the microprocessor 25 returns to step s114.

Once the FAT key 18 has been pressed, the microprocessor 25 performs another number entry step, step s116. This enables the user to enter the quantity in grams of fats for the food item. At step s117, the microprocessor 25 determines whether the CLEAR key 21 is being pressed. If the CLEAR key 21 is not being pressed, the microprocessor 25 performs step s121 to determine whether the fiber (FIBER) key 50 is being pressed. If the fiber (FIBER) key 50 is not being pressed, the microprocessor 25 returns to step s117.

Once the fiber (FIBER) key 50 has been pressed, the microprocessor 25 performs another number entry step, step s122. This enables a user to enter the quantity in grams of dietary fiber for the food item. At step s123, the microprocessor 25 determines whether the CLEAR key 21 is being pressed. If the CLEAR key 21 is not being pressed, the microprocessor 25 performs step s118 to determine whether the POINTS key 19 is being pressed. If the POINTS key 19 is not being pressed, the microprocessor 25 returns to step s123. If, however, the POINTS key 19 is being pressed, the microprocessor 25 performs step s119. At step s119, the microprocessor 25 calculates the POINTS for the food item according to the equation:

$$p = \frac{c}{50} + \frac{f}{12} - \frac{r}{5}$$

where p is the POINTS value, c is the number of kilocalories entered, f is the number of grams of fat entered and r is the number of grams of dietary fiber entered. The microprocessor 25 then causes the display driver 33 to display the POINTS value on the display 5.

Once the POINTS value has been displayed, the microprocessor 25 moves to step s109. If, for instance, the displayed POINTS value is greater than the POINTS left for the use for the current day, the user may not eat the food item and can press the CLEAR key 21.

After step s120 is performed, the microprocessor 25 reenters the loop of steps s102, s103 and s104.

The skilled person will appreciate that many variants of the present invention are possible. For instance, the process of the present invention may employ a calculator provided with an alphanumeric keyboard and be programmable to allow a user to enter all or part of a word for searching the database. Additionally, a user could use the keyboard to add records to the database. The art of calculators includes many techniques for updating stored data and the skilled person will readily see how these might be applied to the present invention.

The skilled person will also appreciate that a calculator, used in the process of the present invention, may have a subset of the features of the described embodiments. For example, the storing of the target and "POINTS left today" values may be omitted.

Furthermore, the features of the second and third calculator embodiments may be combined in a single calculator.

It will also be appreciated that the process of the present invention may be manually implemented by measuring the various quantities, calculating point values by hand, determining daily point ranges and selecting and ingesting food servings having a total point value within said range, all done without resort to a specialized calculator. Moreover, the step of measuring properties of candidate foods and/or calculating point values may be performed, for example, by diet plan organizers or food packagers, and provided to individuals participating in a weight control program.

Another alternative embodiment of the present invention involves the use of a slide rule calculated in accordance with the appropriate point algorithm. Such a slide rule, incorporating the algorithm of equation 1, where $k_1=50$, $k_2=12$ and $k_3=5$, is shown in FIG. 8(*a*).

Figure 8A:
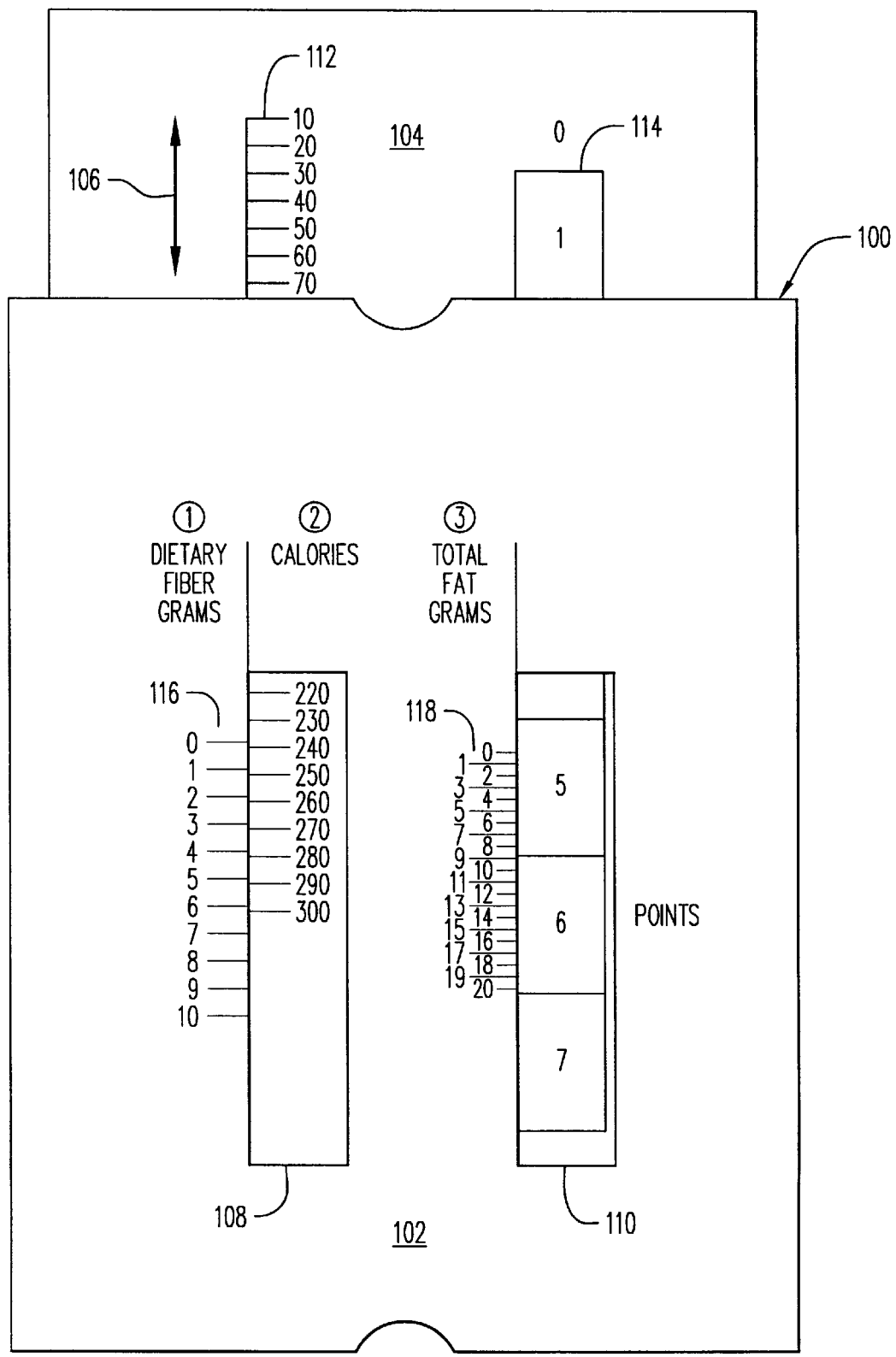
FIGS. 8(a), (b) and (c) relate to a slide rule for obtaining POINT values for practicing the present invention.
Figure 8B:
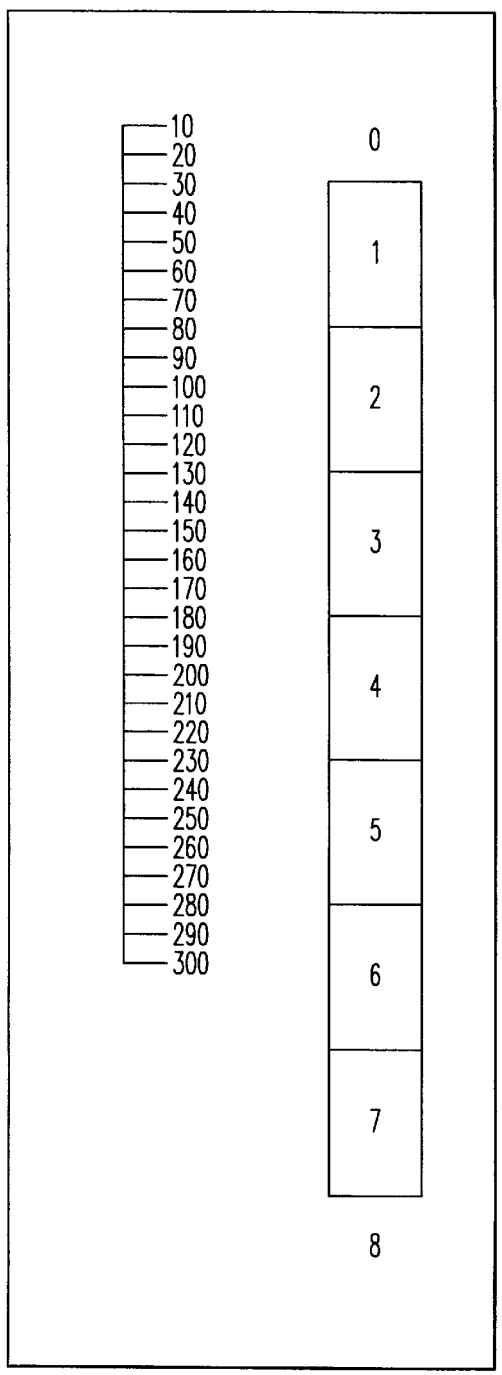
Figure 8C:
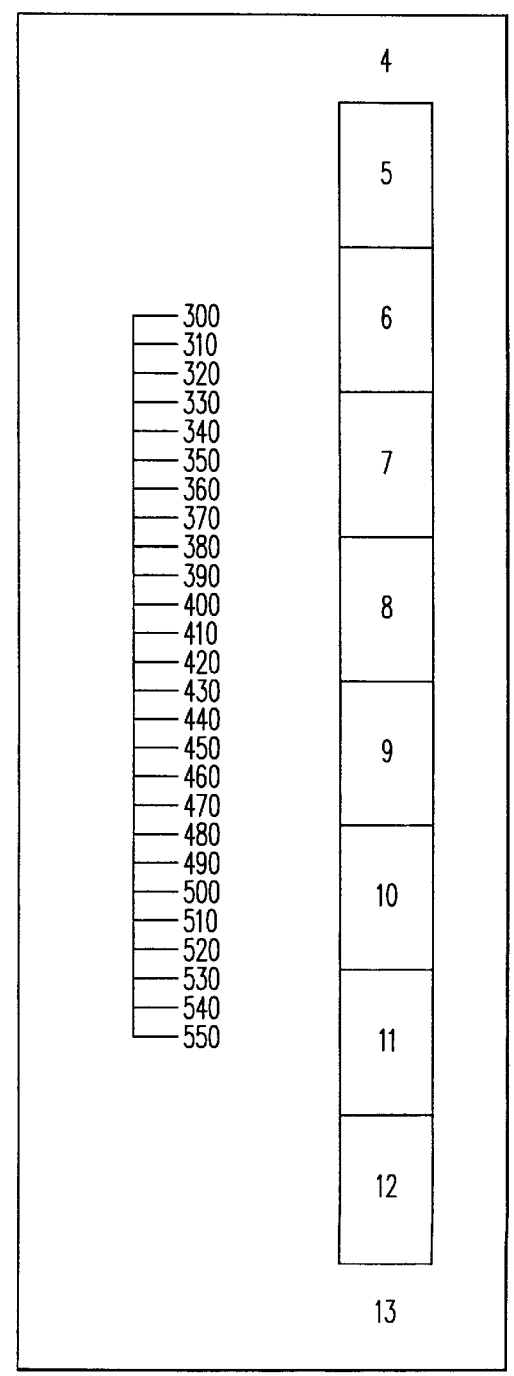

In FIG. 8(*a*), a slide rule 100 consists of a sleeve 102 and a slider 104 moveable within said sleeve in the directions indicated by double-headed arrow 106. Windows 108 and 110 in the sleeve 102 provide views to calorie scale 112 and point scale 114 printed on the slider 104. The arrangement of the scales on the front and back of the slider 104 are shown in FIGS. 8(*b*) and 8(*c*), respectively.

In operation, the user first determines the values of dietary fiber in grams, calories and total fat in grams for a candidate food serving. The slider 104 is then moved until the calories scale 112 is aligned with the dietary fiber measurement on the dietary fiber scale 116 on the sleeve 102. Total fat in grams is then located on the fat scale 118. The number of POINTS for the food serving is then read in window 110 opposite the total fat for the serving. If calories per serving are more than 300, the slide is removed, turned over and reinserted to complete the calculation.

Thus, for example, if values of c=270, r=4 and f=14 were used, the slide rule would provide a value of 6 POINTS for the food serving.

While the present invention has been exemplified by numerous embodiments, the scope of the invention is intended to be defined by the following claims and their equivalents recognized under law.

We claim:

1. A process for reducing body weight in a human being comprising the steps of
    (a) measuring the number of kilocalories, c, in the candidate food servings;
    (b) measuring the total amount of fat, f, in the candidate food servings;
    (c) measuring the amount of dietary fiber, r, in the candidate food serving;
    (d) calculating a whole number point value p for each candidate food serving in accordance with the equation $$p = \frac{c}{k_1} + \frac{f}{k_2} - \frac{r}{k_3}$$

wherein $k_1$, $k_2$ and $k_3$ are preselected constants; wherein $k_2$ is in the range $k_1/4.5$ to $k_1/1.5$ when f is measured in grams; and wherein $k_3$ is in the range of $k_1/20$ to $k_1/5$, when r is measured in grams;
    (e) determining a range of points allotted per day based on current body weight and caloric reduction to be achieved;
    (f) during a day, selecting and ingesting food servings having a total point value within said range; and
    (g) repeating at least step (f) in successive days until the desired weight reduction is achieved.

2. The process of claim 1, wherein $k_1=50$, $k_2=12$ and $k_3=5$, where f and r are measured in grams.

3. The process of claim 2, wherein the range of points allotted per day is seven points from minimum to maximum.

4. The process of claim 3, wherein the range of points allotted per day is determined in accordance with the following table:

| Current Body Weight | Range Of POINTS Allotted Per Day |
| --- | --- |
| Less than 150 pounds | 18–25 |
| 150 to 174 pounds | 20–27 |
| 175 to 199 pounds | 22–29 |
| 200 to 224 pounds | 24–31 |
| 225 to 250 pounds | 26–33 |
| Over 250 pounds | 28–35. |

5. The process of claim 4, wherein food servings having a total number of points equal to the minimum are ingested each day and wherein unused points up to the maximum may be carried over to another day within the week.

6. The process of claim 1, wherein points are added to the maximum number determined for a particular day in step (e) on the basis of the performance of physical exercise during that day.

7. The process of claim 1, wherein the point values of step (d) are calculated by the individual whose weight is to be reduced.

8. The process of claim 1, wherein the calculation of step (d) is performed electronically in a computing device having a memory including parameters necessary to make said calculation.

9. The process of claim 1, wherein the calculation of step (d) is performed with a slide rule calibrated in accordance with the equation of step (d).

10. The process of claim 1, wherein whole number point values, calculated in accordance with the equation of step (d), are provided in tabular form for serving sizes specified in readily estimatable units.

11. The process of claim 1, wherein whole number point values calculated in accordance with the equation of step (d) are printed on the packaging of the food serving.

12. The process of claim 1, wherein the step of selecting food servings for ingestion includes selecting a minimum number of servings of milk products and of fruits and vegetables.

13. A process for weight control comprising the steps of:

determining a single whole number numerical point value for each of a variety of food servings approximately equal to the calories in the food serving divided by 50, the point value being increased by about one point for each 12 grams of fat content and reduced by about one point for each 5 grams of dietary fiber content of the serving;

measuring the current weight of an individual and determining therefrom a minimum and maximum whole number daily point total between 18 and 35 appropriate to produce a restricted daily calorie intake for the individual;

identifying candidate food servings for a day's menu;

selecting food servings such that the sum of the numerical point values for such food servings lies within the determined minimum and maximum; and ingesting the food servings selected.

14. The process of claim 15, wherein the point value, p, for each food serving is determined using a slide rule calibrated in accordance with the equation $$p = \frac{c}{50} + \frac{f}{12} - \frac{r}{5}$$

where c is kilocalories, f is total fat content in grams and r is dietary fiber in grams.

15. The process of claim 13, wherein said point value is determined by a calculator in accordance with a formula of the form $$p = \frac{c}{k_1} + \frac{f}{k_2} - \frac{r}{k_3}$$

where c is calories, f is fat in grams and r is dietary fiber in grams for each candidate food serving and where $k_1$ is about 12 and $k_3$ is about 5.

16. The process of claim 15, wherein said steps are performed by entering values for f, c and r into the calculators entering values for the maximum and minimum daily point total; and displaying on said calculator a value for POINTS left.

17. A process for weight control comprising the steps of:

storing data in a computer memory from which can be obtained a numerical whole number point value for each of a variety of food servings based on the calories, fat and dietary fiber content of the serving wherein each numerical point value is based on a predetermined fraction of the energy content of the food serving increased on the basis of fat content and decreased on the basis of fiber content;

obtaining said numerical whole number point value for candidate food servings for a day's menu;

determining a minimum and maximum whole number numerical daily point total appropriate to produce a restricted daily energy intake based on the current weight of the individual;

calculating the sum of the numerical point values for said candidate food servings;

determining whether the calculated sum lies within the determined minimum and maximum; and ingesting the food servings corresponding to a total lying within said determined minimum and maximum.

* * * * *